US005756783A

United States Patent [19]
Knutson et al.

[11] Patent Number: 5,756,783
[45] Date of Patent: May 26, 1998

[54] 1α-HYDROXY-24-EPI-VITAMIN D₄

[75] Inventors: Joyce C. Knutson, Madison, Wis.; Robert M. Moriarty; Raju Penmasta, both of Oak Park, Ill.; Charles W. Bishop, Verona, Wis.

[73] Assignee: Bone Care International, Inc., Madison, Wis.

[21] Appl. No.: 524,889

[22] Filed: Sep. 7, 1995

Related U.S. Application Data

[62] Division of Ser. No. 261,730, Jun. 17, 1994, abandoned, which is a continuation of Ser. No. 827,173, Jan. 29, 1992, abandoned, which is a continuation-in-part of Ser. No. 800,045, Nov. 29, 1991, abandoned, which is a continuation of Ser. No. 586,854, Sep. 21, 1990, abandoned.

[51] Int. Cl.⁶ .................................................. C07C 401/00
[52] U.S. Cl. .................................................. 552/653
[58] Field of Search .................................................. 552/653

[56] References Cited

U.S. PATENT DOCUMENTS

| | | |
|---|---|---|
| 3,880,894 | 4/1975 | DeLuca . |
| 4,338,250 | 7/1982 | DeLuca et al. . |
| 4,554,105 | 11/1985 | Hesse ............................. 260/397.2 |
| 4,554,106 | 11/1985 | DeLuca et al. .................. 260/397.2 |
| 4,719,204 | 1/1988 | DeLuca et al. . |
| 4,758,383 | 7/1988 | Tachibana ........................ 552/653 |
| 4,769,181 | 9/1988 | DeLuca et al. . |
| 4,927,815 | 5/1990 | DeLuca et al. .................. 514/167 |
| 4,973,584 | 11/1990 | DeLuca et al. . |
| 5,354,744 | 10/1994 | DeLuca et al. .................. 552/653 |

FOREIGN PATENT DOCUMENTS

| | | |
|---|---|---|
| 9205130 | 4/1992 | WIPO . |
| WO 92/05130 | 4/1992 | WIPO . |

OTHER PUBLICATIONS

R. Pardo and M. Santelli, "Synthèse des Métabolites de la Vitamine D," *Bulletin de la Société Chimique de France*, No. 1, 1985, pp. 98–114 (Document is in French, no English translation).

P. J. Kocienski et al., "Synthesis of 53 Using Two Chiral Building Blocks, One Obtained by Partial Synthesis and One Prepared Using a Chirality Inducing Reaction," *Synform*, vol. 3, No. 2, May 1985, pp. 75–76.

A. V. Andreev et al., "Products of the Photoconversion of Provitamin D₄ Obtained From Mutants of Yeast (Saccaromyces Cerevisiae). I. Irradiation in Ethanol," p. 333; col. 1; abstract *Khim. Prir. Soedin.*, No. 2, 1989, pp. 247–254, (Russ.) *Chemical Abstracts*, vol. 111, No. 13, 25 Sep. 1989, Abstract No. 111630k (English abstract).

E. Braunwald et al., *Harrison's Principles of Internal Medicine*: Part Eleven, "Disorders of Bone and Mineral Metabolism," Chapter 335, McGraw–Hill, New York, 1987, pp. 1860–1865.

Grab, W., *Z. Physiol. Chem.*, 243:63–89 (1936).

McDonald, F. G., *J. Biol. Chem.*, 114:IVX (1936).

Windaus, A. and Trautmann, G., *Z. Physiol. Chem.*, 247:185–188 (1937).

*Merck Index*, S. Budavari (ed.), 11th ed., Merck & Co., Rahway, N.J. (1989) pp. 1579, #9930.

DeLuca et al., *Arch. Biochem, Biophys.*, 124:122–128 (1968).

Tarzia et al., *Gazz. Chim. Ital.*, 97:102–106 (1967).

Morris & Boyd, *Organic Chemistry*, 4th ed. pp. 248–249 (1983).

Pardo, et al, *Bull Soc Chem France*, pp. II 98–114 (1985).

Quinkert, eds., *Synform*, pp. 75–76 (1985).

Chems Abs 111:111630k (1989).

*Primary Examiner*—Kimberly J. Prior
*Attorney, Agent, or Firm*—Teresa J. Welch; Stroud, Stroud, Willink, Thompson & Howard

[57] ABSTRACT

1α-Hydroxy-24-epi-vitamin D₄ and novel intermediates formed in a novel method of preparing this compound. The method includes campesterol as a starting material which is converted to 24-epi-vitamin D₄ which is in turn hydroxylated to 1α-hydroxy-24-epi-vitamin D₄ via tosylated and cyclic derivatives of 24-epi-vitamin D₄. 1α-Hydroxy-24-epi-vitamin D₄ has been found to be bioactive.

4 Claims, 2 Drawing Sheets

1α-HYDROXY-24-EPI-VITAMIN D$_4$

This is a division of application Ser. No. 08/261,730 filed Jun. 17, 1994, now abandoned, which is a continuation of application Ser. No. 07/827,173, filed Jan. 29, 1992, now abandoned, which is a continuation-in-part of application Ser. No. 07/800,045 filed Nov. 29, 1991, now abandoned, which is a continuation of application Ser. No. 07/586,854, filed Sep. 21, 1990, now abandoned.

TECHNICAL FIELD

This invention relates to biologically active vitamin D$_4$ compounds. More specifically, this invention relates to novel 1α-hydroxy-24-epi-vitamin D$_4$ and a method for preparing this compound as well as novel intermediates formed in the synthesis.

BACKGROUND

The vitamins D are a group of compounds that are steroid derivatives and are known to be important in the regulation of calcium metabolism in animals and man. See, *Harrison's Principles of Internal Medicine*: Part Eleven, "Disorders of Bone and Mineral Metabolism, Chapter 335," E. Braunwald et al., (eds.), McGraw-Hill, New York, 1987, pp. 1860–1865.

The naturally occurring form of vitamin D in animals and man is vitamin D$_3$. Vitamin D$_3$ is synthesized endogenously in the skin of animals and man. In animals, including man, vitamin D$_3$ is activated by being hydroxylated in the C$_{25}$ position in the liver, followed by 1α-hydroxylation in the kidney to produce the hormone 1α,25-dihydroxy vitamin D$_3$. See, U.S. Pat. No. 3,880,894.

1α,25-Dihydroxy vitamin D$_3$ is the hormonally active form of vitamin D$_3$. This hormone is taken up in the intestine by specific cytoplasmic receptor proteins to stimulate calcium and phosphate transport from the intestinal lumen to circulation. The vitamin D$_3$ hormone also is taken up by specific cytoplasmic receptors in the parathyroid glands, the kidney, the osteoblasts, and other target tissues, to elicit cellular responses which, synergistically, stabilize blood levels of calcium and phosphorus, control the formation and removal of bone, and regulate the further production of 1α,25-dihydroxy vitamin D$_3$ itself. It is now recognized that the 1α-hydroxy group is important in the binding of 1α,25-dihydroxy vitamin D$_3$ with its specific cytoplasmic receptors. It has also recently been reported that the vitamin D$_3$ hormones may play a role in cell proliferation and differentiation.

Vitamin D$_2$ is the major, naturally occurring form of vitamin D found in plants. Vitamin D$_2$ differs structurally from vitamin D$_3$ in that vitamin D$_2$ has a methyl group at C$_{24}$ and has a double bond between C$_{22}$ and C$_{23}$.

Considerable interest has focused on discovery and synthesis of various hydroxylated and dihydroxylated derivatives of vitamins D$_3$ and D$_2$. Examples of hydroxylated and dihydroxylated metabolites of vitamins D$_3$ and D$_2$ which have been found to occur naturally and/or have been synthesized include 25-hydroxy vitamin D$_2$, 24, 25-dihydroxy vitamin D$_3$, 25, 26-dihydroxy vitamin D$_3$, 1α-hydroxy vitamin D$_2$, 23, 25-dihydroxy vitamin D$_3$, all of which have been found to exhibit vitamin D-like biological activity in vivo.

Unfortunately, while many of these active vitamin D metabolites held great promise as therapeutic agents, this promise has never been fully realized because of the extreme toxicity of these agents. For example, toxicity limits the efficacy of vitamin D$_3$, its active forms and analogs, to prevent bone loss or restore lost bone. Many studies indicate that at dosages required for these agents to be effective in bone loss prevention or restoration, hypercalcemia and hypercalciuria are serious problems. It has been reported that 1α-hydroxy vitamin D$_3$ at a daily dose of 2 μg/day (which has been shown in some studies to be effective in preventing loss of bone) causes toxicity in approximately 67 percent of patients.

Vitamin D$_4$ is a little known form of vitamin D. Vitamin D$_4$ was first described in 1936. See, Grab, W., *Z. Physiol. Chem.*, 243:63 (1936); McDonald, F. G., *J. Biol. Chem.*, 114:IVX (1936). See also, Windaus, A. and Trautmann, G., *Z. Physiol. Chem.*, 247:185–188 (1937). Vitamin D$_4$, also known as irradiated 22,23-dihydro-ergosterol or 22,23-dihydro vitamin D$_2$ or 22,23-dihydro-ergocalciferol, differs from vitamin D$_3$ in that it contains a C$_{24}$ methyl group. The above cited references disagree as to the level of biological activity of this D vitamin, suggesting that in the rat, vitamin D$_4$ is one-third or three-fourths as active as vitamin D$_3$, and in the chick, either one-tenth or one-fifth as active as vitamin D$_3$.

In 1968, DeLuca et al. (*Arch. Biochem. Biophys.*, 124:122–128 (1968)) confirmed that vitamin D$_4$ was less active than vitamin D$_3$. DeLuca et al. reported that vitamin D$_4$ is two-thirds as active as vitamin D$_3$ or vitamin D$_2$ in the rat, and one-fifth as active as vitamin D$_3$ in the chick.

DeLuca et al. make reference to the fact that "[t]he synthesis of vitamin D$_4$ has apparently been little used since it was first described by Windaus and Trautmann," and comment, "[t]his is perhaps due to the fact that vitamin D$_4$ is only of academic interest."

To applicants' knowledge, vitamin D$_4$ has remained "only of academic interest" as applicants are unaware of any further study of vitamin D$_4$ since that reported by DeLuca et. al. In fact, *The Merck Index* states with respect to vitamin D$_4$, "[i]ts biological activity seems doubtful." *Merck Index*, S. Budavari (ed.), 11th ed., Merck & Co., Rahway, N.J., (1989) pp. 1579, #9930.

There has been even less interest in vitamin D$_4$ analogues. Recently, however, a vitamin D$_4$ analogue, 1α-hydroxy vitamin D$_4$, has been synthesized and shown to possess unexpectedly high biopotency and low toxicity (co-pending U.S. patent application Ser. No. 07/586,854, filed Sep. 21, 1990). It was surprising to applicants in that application that this vitamin D$_4$ analogue had activity commensurate with the vitamin D$_3$ and D$_2$ hormones. Applicants, in this invention, have synthesized a related isomer of 1α-hydroxy vitamin D$_4$ with equally surprising biological activity.

SUMMARY OF THE INVENTION

The present invention provides a stereoisomer of vitamin D$_4$, 1α-hydroxy-24-epi-vitamin D$_4$, tosylated and cyclic derivatives of this compound, and a method of preparing these compounds.

In one aspect, the invention provides the compounds of formula (I) as defined hereinbelow. 1α-Hydroxy-24-epi-vitamin D$_4$, the compound of formula (I) wherein R$_1$ and R$_2$ are each hydroxy groups, has been found to be bioactive. Other compounds encompassed by formula (I) have been found to be novel intermediates in the synthesis of 1α-hydroxy-24-epi-vitamin D$_4$.

In another aspect, the invention provides the compounds of formula (II) which have also been found to be novel intermediates in the synthesis of 1α-hydroxy-24-epi-vitamin D$_4$.

In further aspect, the invention provides a synthetic route for making the 1α-hydroxy-24-epi-vitamin $D_4$. The method includes campesterol as a starting material which is converted to 24-epi-vitamin $D_4$ which is in turn hydroxylated to 1α-hydroxy-24-epi-vitamin $D_4$ via tosylated and cyclic derivatives of 24-epi-vitamin $D_4$. A novel intermediate which is a derivative of campesterol has also been found.

Other advantages and a fuller appreciation of the specific invention, compositional variations, and physical and chemical attributes of the present invention will be gained upon an examination of the following detailed description of the invention, taken in conjunction with the accompanying drawings.

BRIEF DESCRIPTION OF THE DRAWINGS

The present invention will hereinafter be described in conjunction with the appended drawings, wherein like designations refer to like elements throughout and in which.

DETAILED DESCRIPTION

The present invention provides synthetic 1α-hydroxy-24-epi-vitamin $D_4$ (1α-OH-24-epi-$D_4$) as well as tosylated and cyclic derivatives of this compound.

As used herein, the terms "biological activity" or "biologically active" are meant to refer to biochemical properties of compounds such as affecting metabolism, e.g., affecting serum calcium concentration, or binding to an appropriate receptor protein, e.g., binding to vitamin D receptor protein. The term "epi" as used herein and as used generally in the art is meant to designate a different absolute configuration about a carbon atom, in the present invention, about the $C_{24}$ carbon, than in the parent vitamin $D_4$ structure.

In one of its aspects, the invention encompasses the compounds of the general formula (I):

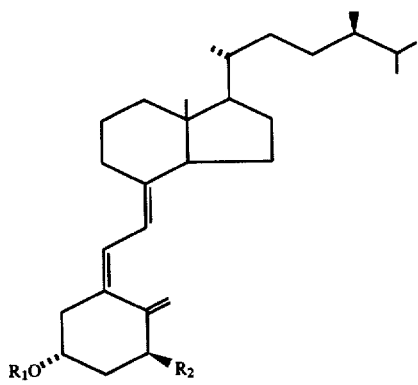

wherein $R_1$ is hydrogen or tosyl and $R_2$ is hydrogen or hydroxy, and salts, hydrates and solvates thereof. Preferred among those compounds of formula (I) is that in which $R_1$ is hydrogen and $R_2$ is OH, i.e., 1α-hydroxy-24-epi-vitamin $D_4$, which has been found to increase serum calcium.

In another aspect, the invention provides compounds of formula (II):

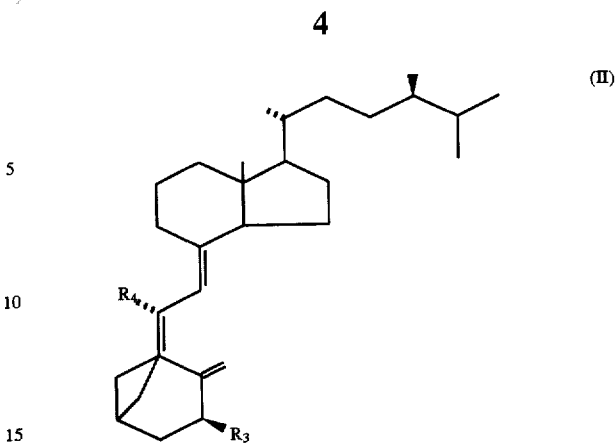

wherein $R_3$ is either hydrogen or hydroxy, and $R_4$ is methoxy, and salts, hydrates and solvates thereof. These compounds have been found to be useful and novel intermediates to form 1α-hydroxy-24-epi-vitamin $D_4$.

Figure 1:
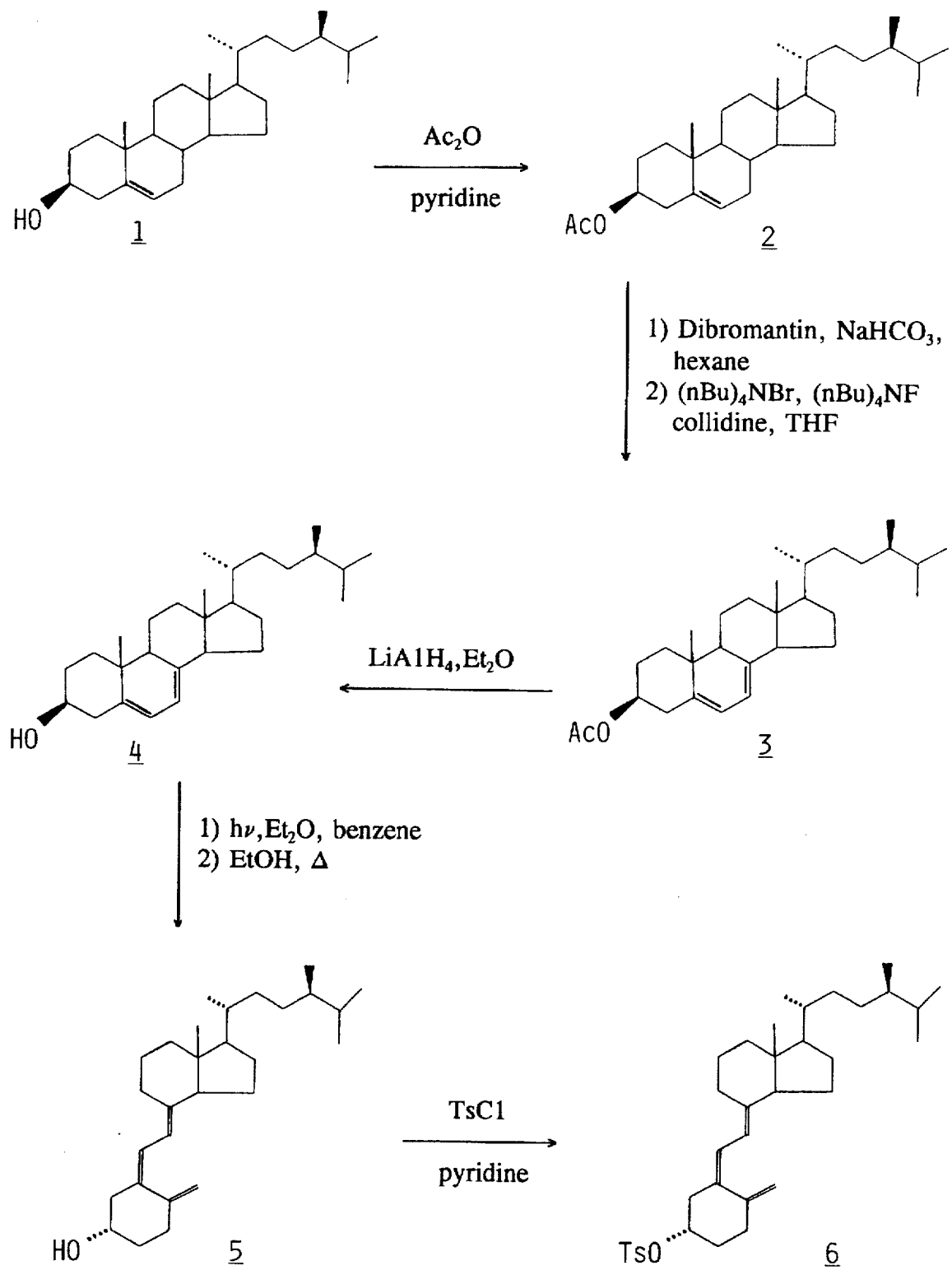
FIG. 1 illustrates preparative steps for the synthesis of 24-epi-vitamin $D_4$ starting with campesterol.
Figure 2:
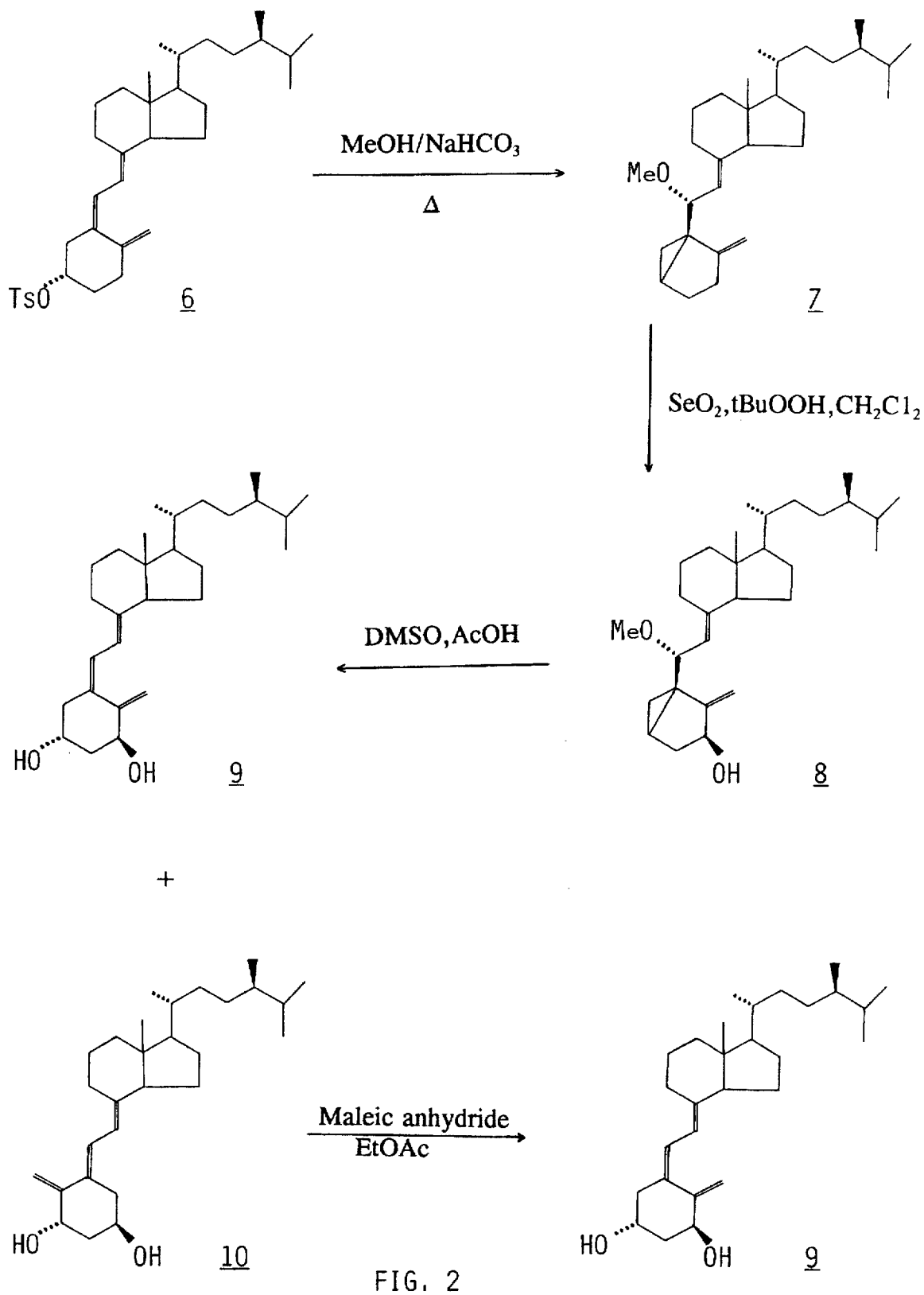
FIG. 2 illustrates preparative steps for the synthesis of 1α-hydroxy-24-epi-vitamin $D_4$ starting with 24-epi-vitamin $D_4$.

In still another aspect, the invention involves the preparation of compounds of formulas (I) and (II) as well as another novel intermediate. Specifically, the synthesis of 1α-hydroxy-24-epi-vitamin $D_4$, i.e., the compound of formula (I) wherein $R_1$ is hydrogen and $R_2$ is OH, is accomplished according to the schema presented in FIGS. 1 and 2. As seen in FIG. 1, the synthesis uses the steroid campesterol as the starting material. Campesterol is available according to the procedure of Tarzia et al., Gazz. Chem. Ital., vol. 97, pp. 102–106 (1967). Campesterol undergoes $C_7$ bromination, $C_7$–$C_8$ dehydrobromination in a four-step process to yield 7-dehydrocampersterol. The 7-dehydrocampesterol is then irradiated and thermally converted by methods well known in the art to yield 24-epi-vitamin $D_4$ [also known as 22,23-dihydro-24-epi-ergocalciferol]. As seen in FIG. 2, 24-epi-vitamin $D_4$ is then hydroxylated in a five-step process to yield 1α-hydroxy-24-epi-vitamin $D_4$.

Specifically, campesterol is acetylated to form the 3β-acetate. This campesterol acetate is subjected to $C_7$ bromination, $C_7$–$C_8$ dehydrobromination to form a double bond at $C_7$–$C_8$. The resulting 7-dehydrocampesterol acetate is then reduced to the novel 7-dehydrocampesterol. The 7-dehydrocampesterol is then irradiated and thermally converted to yield 24-epi-vitamin $D_4$. The 24-epi-vitamin $D_4$ is then tosylated to yield the 3β-tosylate of 24-epi-vitamin $D_4$. The tosylate is displaced by solvolysis to yield the 6-methoxylate of 24-epi-3,5-cyclovitamin $D_4$.This 24-epi-cyclovitamin $D_4$ is subjected to allylic oxidation to form the 1α-hydroxy 24-epi-cyclovitamin derivative. The 1α-hydroxy 24-epi-cyclovitamin derivative is sequentially hydrolyzed and subjected to a Diels-Alder type reaction which removes the 6-methoxy group and separates the 1α-hydroxy 24-epi-vitamin $D_4$ (5,6 cis) from the 5,6 trans 1α-hydroxy 24-epi-vitamin $D_4$. It is noted that the trans isomer, if desired, may be separated from the cis isomer via high pressure liquid chromatography according to the procedure disclosed, for example, in U.S. Pat. No. 4,719,204 issued to DeLuca et al.

1α-Hydroxy-24-epi-vitamin $D_4$ has been found to possess physiological activity, namely, as an agent for increasing serum calcium concentrations. Specifically, this compound increases serum calcium concentrations in rats with vitamin D deficiency. Thus, the compounds of the invention are potentially applicable to various clinical and veterinary fields, and are particularly useful for the treatment of abnormal metabolism of calcium and phosphorus.

The following examples are to be construed as merely illustrative, and not limitative of the remainder of the disclosure in any way whatsoever. In the following examples, all temperatures are set forth in degrees Celsius; unless otherwise indicated, all product yields are reported as percentages by weight. Proton nuclear magnetic resonance ($^1$H NMR) spectra were recorded with a Bruker AM—400 (400 MHz) with aspect 3000 Computer in $CDCl_3$ solutions with $CHCl_3$ as an internal standard. Chemical shifts are reported in ppm. Ultraviolet spectra were recorded with a Hitachi U-2000 Spectrophotometer and are reported for ethanol solutions.

EXAMPLE 1: Synthesis of 1α-hydroxy-24-epi-vitamin $D_4$

Campesterol Acetate (2):

To a solution of 24.0 g (0.06 mol) of campesterol (1) in 180 ml of anhydrous pyridine was added 18.5 ml (0.196 mol) of acetic anhydride. The mixture was stirred at room temperature overnight and then 600 ml of water was added. The precipitate was filtered and washed three times with 200 ml portions of acetonitrile, and then air dried to yield 20.0 g (75%) of (2).

$^1$H NMR: (400 MHz, $CDCl_3$); δppm 0.7 (3H, s, 18-$CH_3$), 0.8 (6H, dd, 26 and 27-$CH_3$), 0.86 (3H, d, 21-$CH_3$), 0.92 (3H, d, 28-$CH_3$), 1.02 (3H, s, 19-$CH_3$), 2.04 (3H, s, $OCOCH_3$), 4.6 (1H, m, 3-H), 5.38 (1H, m, 6-H).

7-Dehydrocampesterol Acetate (3)

A mixture of 10 g (0.023 mol) of (2), 4.56 g (0.016 mol) of dibromantin and 10.2 g (0.121 mol) of anhydrous sodium bicarbonate in 250 ml of dry hexane was heated under reflux in a nitrogen atmosphere for 2 hrs. The precipitate was filtered off and the solution was concentrated to dryness under reduced pressure. To the solution of the residue in 50 ml of anhydrous tetrahydrofuran was added 0.65 g (2.02 mmol) of tetrabutylammonium bromide, and the mixture was stirred at room temperature for 30 min under nitrogen. A solution of tetrabutylammonium fluoride (112 ml, 1M in THF) was then added followed by 5.0 ml of s-collidine, and the mixture was stirred under nitrogen at room temperature overnight. To this reaction mixture was added ether (700 ml), and the organic phase was washed with water (2×200 ml), cold 1M HCl (2×200 ml) and 10% sodium bicarbonate (2×200 ml), and dried over anhydrous $MgSO_4$. Chromatography on silica gel with 10% ethyl acetate in hexane gave 5.5 g (55%) of (3).

$^1$H NMR: (400 MHz, $CDCl_3$); δppm 0.62 (3H, s, 18-$CH_3$), 0.80 (6H, dd, 26 and 27-$CH_3$), 0.86 (3H, d, 21-$CH_3$), 0.94 (3H, d, 28-$CH_3$), 0.96 (3H, s, 19-$CH_3$), 2.05 (3H, s, $OCOCH_3$), 4.7 (1H, m 3-H), 5.4 (1H, m, 7-H), 5.58 (1H, m, 6-H).

7-Dehydrocampesterol (4)

To a solution of 5.5 g (0.012 mol) of (3) in dry ether (500 ml) was added 3.38 g (0.089 mol) of lithium aluminum hydride. The mixture was stirred at room temperature for 2 hours, cooled with an ice water bath, and the reaction mixture decomposed by the cautious dropwise addition of ice water (5 ml). The mixture was filtered and the filtrate was concentrated in vacuo to remove most of the tetrahydrofuran. The residue was dissolved in 1000 ml of ether and washed with saturated NaCl solution (2×500 ml), dried over anhydrous $MgSO_4$ and concentrated in vacuo. The residue was purified on a silica gel column using 20% ethyl acetate in hexane to yield 4.0 g (80%) of (4).

$^1$H NMR: (400 MHz, $CDCl_3$); δppm 0.62 (3H, s, 18-$CH_3$), 0.8 (6H, dd, 26 and 27-$CH_3$), 0.86 (3H, d, 21-$CH_3$), 0.94 (3H, d, 28-$CH_3$), 0.96 (3H, s, 19-$CH_3$), 3.62 (1H, m, 3-H), 5.39 (1H, m, 7-H), 5.58 (1H, m, 6-H).

24-epi-Vitamin $D_4$ (5)

7-Dehydrocampesterol (4) (3.0 g, 7.5 mmol) was dissolved in 500 ml of ether and benzene (4:1) and irradiated with stirring under nitrogen in a water-cooled quartz immersion well using a Hanovia medium-pressure UV lamp for 1.5 hrs. The solution was concentrated in vacuo, redissolved in 200 ml of ethanol and heated under reflux overnight. The solution was concentrated to dryness in vacuo and the residue was purified on a silica gel column using 20% ethyl acetate in hexane to yield 0.9 g (30%) of (5).

$^1$H NMR: (400 MHz, $CDCl_3$); δppm 0.54 (3H, s, 18-$CH_3$), 0.76 (6H, dd, 26 and 27-$CH_3$), 0.82 (3H, d, 21-$CH_3$), 0.9 (3H, d, 28-$CH_3$), 3.91 (1H, m, 3-H), 4.7 (1H, m, 19-H), 5.03 (1H, m, 19-H), 6.02 (1H, d, 7-H), 6.21 (1H, d, 6-H). UV (ethanol) $\lambda_{max}$:265 nm.

24-epi Vitamin-$D_4$ tosylate (6)

To a solution of 0.9 g (2.26 mmol) of (5) dissolved in 10 ml of anhydrous pyridine was added 1.2 g (6.30 mmol) of tosyl chloride. The mixture was stirred under nitrogen at 5° C. for 24 hrs. The reaction mixture was poured into 100 ml of cold saturated $NaHCO_3$ solution and extracted with ether (3×200 ml). The combined ether extracts were washed with 5% HCl solution (3×300 ml), saturated sodium bicarbonate solution (3×300 ml) and saturated NaCl solution (2×300 ml), dried over anhydrous $MgSO_4$ and concentrated in vacuo to yield 1.1 g (88%) of (6).

24-epi-3,5-Cyclovitamin $D_4$ (7)

To a solution of 1.0 g (1.81 mmol) of (6) dissolved in 100 ml of anhydrous methanol was added sodium bicarbonate 10.0 g (0.12 mol). The mixture was heated under reflux for 8 hrs. The reaction mixture was concentrated in vacuo. Water (200 ml) was added followed by extraction with ether (3×300 ml). The combined ether extracts were dried over anhydrous $MgSO_4$ and concentrated to dryness in vacuo to yield 600 mg (80%) of (7) as an oil.

1H NMR: (400 MHz, $CDCl_3$); δppm 0.54 (3H, s, 18-$CH_3$), 0.78 (6H, dd, 26 and 27-$CH_3$), 0.86 (3H, d, 21-$CH_3$), 0.92 (3H, d, 28-$CH_3$), 3.25 (3H, s, 13 $OCH_3$), 4.16 (1H, d, 6-H), 4.86 (1H, m, 19-H), 4.98 (1H, d, 7-H), 5.02 (1H, m, 19-H).

1α-Hydroxy-24-epi-3,5-cyclovitamin $D_4$ (8)

tert-Butyl hydroperoxide (1.13 ml, 3.39 mmol; 3M in toluene) was added to a suspension of 95 mg (0.86 mmol) of selenium dioxide in 65 ml of anhydrous dichloromethane under nitrogen. The mixture was stirred at room temperature under nitrogen for 3 hours. Then 0.13 ml of anhydrous pyridine was added followed by a solution of 600 mg (1.45 mmol) of (7) dissolved in 20 ml of anhydrous dichloromethane. The mixture was stirred under nitrogen at room temperature for 15 min, then 25 ml of 10% NaOH solution was added and the mixture was extracted with ether (3×100 ml). The combined ether extracts were washed with 10% NaOH solution (3×100 ml), water (3×100 ml), saturated sodium chloride solution (2×100 ml), dried over anhydrous $MgSO_4$ and concentrated to dryness in vacuo. The residue was purified on a silica gel column using a mixture of 20% ethyl acetate in hexane to yield 140 mg (23%) of (8) as an oil.

$^1$H NMR: (400 MHz, $CDCl_3$); δppm, 0.54 (3H, s, 18-$CH_3$), 0.79 (6H, dd, 26 and 27-$CH_3$), 0.88 (3H, d, 21-$CH_3$), 0.92 (3H, d, 28-$CH_3$), 3.24 (3H, s, —$OCH_3$) 4.2 (1H, m, 3-H), 4.21 (1H, d, 6-H), 4.94 (1H, d, 7-H), 5.15 (1H, m, 19-H), 5.21 (1H, m, 19-H).

5,6-cis and 5,6-trans-1α-hydroxy-24-epi-vitamin D4 (9, 10)

1α-Hydroxy-24-epi-3,5 cyclovitamin $D_4$ (8) (110 mg, 0.26 mmol) was dissolved in 1.1 ml of dimethylsulfoxide and 0.9 ml of acetic acid and heated at 50° C. under nitrogen for 1 hour. The solution was poured over ice and 50 ml of saturated $NaHCO_3$ solution. The mixture was extracted with ether (3×100 ml). The combined ether extracts were washed with saturated NaHCO₃ solution (3×100 ml), water (2×100 ml), and saturated NaCl solution (2×200 ml), dried over anhydrous MgSO₄ and concentrated in vacuo to yield the crude product 105 mg (95%) of (9) and (10).

5,6-cis-1α-hydroxy-24-epi-vitamin D₄ (9) To a solution of (9) and (10), 105 mg (0.25 mmol) in 5 ml of ethyl acetate, was added 20 mg (0.2 mmol) of maleic anhydride, and the mixture was stirred at 35° C. for 24 hours under nitrogen. The solution was concentrated to dryness in vacuo. The residue was purified on a silica gel column using 40% ethyl acetate in hexane to yield 30 mg (28%) of (9).

¹H NMR: (400 MHz, CDCl₃); δppm 0.54 (3H, 1 s, 18-CH₃), 0.78 (6H, dd, 26 and 27-CH₃), 0.86 (3H, d, 21-CH₃), 0.92 (3H, d, 28-CH₃), 4.2 (1H, m, 3-H), 4.41 (1H, m, 1-H), 5.0 (1H, m, 19-H), 5.32 (1H, m, 19-H), 6.0 (1H, m, 7-H), 6.38 (1H, m, 6-H); UV (ethanol) λ$_{max}$:265 nm.

EXAMPLE 2: Biological testing of 1α-hydroxy-24-epi-vitamin D₄

Male weanling rats (Holtzman strain, Holtzman Company, Madison, Wis.) were fed a vitamin D deficient diet containing adequate calcium (0.47%) and phosphorus (0.3%). Within three to four weeks, this diet induces an extreme vitamin D deficiency characterized by low serum calcium and poor growth. After four weeks on this diet, the rats had serum calcium values less than 6 mg/dl. The rats were then separated into four groups and orally administered either 1α-hydroxy-24-epi-vitamin D₄ in a vehicle such as coconut oil or the vehicle (control) for each of 14 days. Twenty-four hours after the last dose, the rats were killed, and the blood calcium measured by a standard laboratory technique. The results of these determinations are shown in Table 1.

TABLE 1

Increase in serum calcium concentration

| Compound | Dose (mcg/kg/day) | Number of Rats | Serum Calcium Concentration (mg/100 ml) ± Standard Deviation |
|---|---|---|---|
| Vehicle | — | 10 | 5.1 ± 0.42 |
| 24-epi-1α-OH-D₄ | 0.042 | 11 | 5.8 ± 0.40 |
| 24-epi-1α-OH-D₄ | 0.250 | 12 | 8.1 ± 1.25 |
| 24-epi-1α-OH-D₄ | 1.500 | 12 | 10.5 ± 0.71 |

The data of Table 1 indicate that 1α-hydroxy-24-epi-vitamin D₄ is effective at increasing serum calcium in the vitamin D deficient rat and that the response appears to be dose dependent.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. The compound of the formula (I):

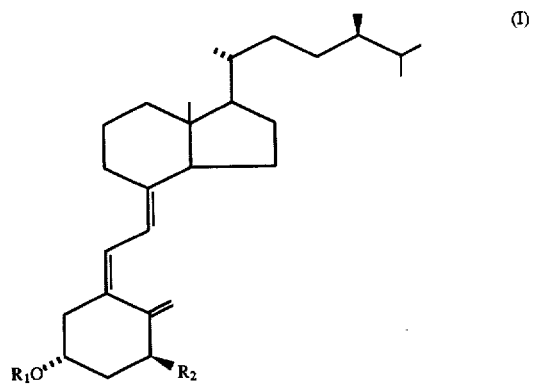

wherein R₁ is either hydrogen or tosyl and R₂ is either hydrogen or hydroxy, or a salt, hydrate, or solvate thereof.

2. The compound of claim 1, wherein the compound is 1α-hydroxy-24-epi-vitamin D₄.

3. 5,6-trans-1α-hydroxy-24-epi-vitamin D₄.

4. 24-epi-vitamin D₄ tosylate.

* * * * *